US000001129H

United States Statutory Invention Registration [19]

[11] Reg. Number: H1129

Gumprecht

[43] Published: Jan. 5, 1993

[54] PROCESS FOR MANUFACTURE OF 1,1,1,2-TETRAFLUOROETHANE

[75] Inventor: William H. Gumprecht, Wilmington, Del.

[73] Assignee: E. I. Du Pont de Nemours and Company, Wilmington, Del.

[21] Appl. No.: 315,295

[22] Filed: Feb. 24, 1989

[51] Int. Cl.[5] ..... C07C 17/00
[52] U.S. Cl. ..... 570/168
[58] Field of Search ..... 570/168

[56] References Cited

U.S. PATENT DOCUMENTS

| | | | |
|---|---|---|---|
| 4,052,470 | 10/1977 | Nychka et al. | 570/168 |
| 4,129,603 | 12/1978 | Bell | 260/653 |

FOREIGN PATENT DOCUMENTS

| | | | |
|---|---|---|---|
| 546962 | 10/1957 | Canada | 570/168 |
| 4966 | 2/1976 | Japan | 570/168 |
| 52-33604 | 8/1977 | Japan . | |
| 2030981 | 3/1983 | United Kingdom . | |

OTHER PUBLICATIONS

Hudlicky in *Chemistry of Organic Fluoride Compounds*, MacMillan Co., New York, NY (1962), p. 98.
Sheppard and Sharts in *Organic Fluorine Chemistry*, W. A. Benjamin, Inc., New York, NY (1969), pp. 76–77.

*Primary Examiner*—Robert L. Stoll
*Assistant Examiner*—Joseph D. Anthony

[57] ABSTRACT

An improved process is disclosed for the manufacture of 1,1,1,2-tetrafluoroethane by the vapor-phase reaction of 2-chloro-1,1,1-trifluoroethane with hydrogen fluoride in the presence of an inorganic chromium (III) catalyst which includes co-feeding molecular chlorine to extend catalyst activity.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR MANUFACTURE OF 1,1,1,2-TETRAFLUOROETHANE

FIELD OF THE INVENTION

This invention relates to an improved process for the manufacture of 1,1,1,2-tetrafluoroethane by the vapor-phase reaction of 2-chloro-1,1,1-trifluoroethane with hydrogen fluoride in the presence of inorganic chromium (III) catalysts.

BACKGROUND OF THE INVENTION

Industrially, fluorinated hydrocarbons are generally prepared by a halogen exchange reaction of halocarbons, such as chlorohydrocarbons or bromohydrocarbons—most usually chlorohydrocarbons, with inorganic fluorine compounds such as alkali metal fluorides, antimony fluorides, silver fluorides and mercury fluorides or with hydrogen fluoride in the presence of a catalyst.

As recognized in the art, the ease with which a halogen exchange reaction occurs depends primarily upon the particular manner in which the halogen atom to be exchanged for fluorine is attached to the carbon atom of the halocarbon. Thus, Hudlicky in *Chemistry of Organic Fluoride Compounds*, MacMillan Co., New York, NY (1962), pg. 98, points out the difficulty of converting the —$CH_2Cl$ group to the —$CH_2F$ group under various reaction conditions. Similarly, Sheppard and Sharts in *Organic Fluorine Chemistry*, W. A. Benjamin, Inc., New York, NY (1969), pp. 76–77, also teach that the Cl radical in the —$CH_2Cl$ group is of very low reactivity and that, when reacted with fluorinating agents, rarely undergoes reaction to provide —$CH_2F$ group.

Furthermore, it is known that fluoro-substitution on a carbon atom adjacent to the —$CH_2Cl$ group reduces the reactivity of the Cl radical of the —$CH_2Cl$ even more. Thus, with the above two unfavorable conditions, to prepare $CF_3CH_2F$ by the vapor-phase reaction of $CF_3CH_2Cl$ with HF requires rather drastic reaction conditions. Bell in U.S. Pat. No. 4,129,603 describes (column 3, lines 55-68) the reaction of $CF_3CH_2Cl$ with HF with an HF to $CF_3CH_2Cl$ ratio of 4:1, a reaction temperature of 350° C. and a contact time of 7 seconds continually over a period of 55 hours using a $Cr_2O_3$ catalyst pretreated with HF. The product stream contained 18.2% $CF_3CH_2F$, 80% unreacted $CH_3CH_2Cl$, 1.65% of a mixture of $CF_3CHF_2$ and $CF_3CH_3$ and 0.12% $CF_2{=}CHCl$. What is not disclosed in the above-cited Bell patent is that in the reaction of $CF_3CH_2Cl$ with HF in the presence of a Cr (III) catalyst at elevated temperatures, with time, the ability of the Cr (III) catalyst to catalyze the halogen exchange reaction is drastically reduced, such that the process becomes useless as an industrial process in a very short time. Depending upon the reaction conditions, the catalyst may become completely inactive in a period of from about 150 to 300 hours.

It is reasonable to speculate that this drastic loss of catalyst activity is due to the rather high temperatures required to make this particular halogen exchange reaction proceed to a reasonable extent. Such elevated temperatures will increase dehydrohalogenation reactions, such as $CF_3CH_2Cl$ to $CF_2{=}CHCl+HF$, and even of the desired product, $CF_3CH_2F$ to $CF_2{=}CHF+HF$. These olefinic compounds can react, particularly on the catalyst surface, to form polymers, carbon or coke deposits which may make the catalyst surfaces unavailable for catalytic activity. Whatever the mechanism, in the reaction of $CF_3CH_2Cl$ and HF over a Cr (III) catalyst at elevated temperatures, the catalyst will rapidly lose activity over a period of time; the higher the reaction temperature the faster will be the loss of activity.

Osaka et al. in British Patent 2,030,981 have recognized the above-discussed loss of activity of the chromium (III) catalyst in the halogen exchange reaction at high temperatures between $CF_3CH_2Cl$ and HF. The patentees suggested introduction into the feed stream of from 0.002 to 0.05 mol $O_2$ per mol of $CF_3CH_2Cl$ to prolong the activity of the Cr (III) catalyst. While co-feeding of $O_2$ with $CF_3CH_2Cl$ prolongs the catalytic activity of Cr (III) catalysts, such modification cannot be used advantageously in an industrial process because of the additional problems it introduces. Among them are greatly increased formation of water in the reaction which increases the difficulty in isolating the desired product, and which greatly increases the corrosion in the condensed phase due to hydrofluoric and hydrochloric acids generated therefrom. Reaction of oxygen with various components of the reaction stream also introduces many undesirable oxygenated by-products.

It is, therefore, an object of the present invention to provide an improved process for manufacturing 1,1,1,2-tetrafluoroethane by the vapor phase reaction of 2-chloro-1,1,1-trifluoroethane with hydrogen fluoride in the presence of an inorganic chromium (III) catalyst. It is a further object of the present invention to provide a process for manufacturing 1,1,1,2-tetrafluoroethane by the vapor phase reaction of 2-chloro-1,1,1-trifluoroethane with hydrogen fluoride in the presence of an inorganic chromium (III) catalyst wherein the activity of the chromium (III) catalyst is maintained.

SUMMARY OF THE INVENTION

In a process for the manufacture of 1,1,1,2-tetrafluoroethane which comprises contacting, in the vapor phase at elevated temperatures, a mixture of 2-chloro-1,1,1-trifluoroethane and hydrogen fluoride with an inorganic chromium (III) catalyst, the improvement comprising co-feeding an effective amount of molecular chlorine with said mixture of 2-chloro-1,1,1-trifluoroethane and hydrogen fluoride.

DETAILED DESCRIPTION OF THE INVENTION

The present improved process for preparing $CF_3CH_2F$ involves co-feeding an effective amount of $Cl_2$ to the reactant stream of 2-chloro-1,1,1-trifluoroethane ($CF_3CH_2Cl$) and HF in the presence of an inorganic Cr (III) catalyst to maintain catalyst activity.

While the present improved process is primarily applicable to the preparation of $CF_3CH_2F$ from $CF_3CH_2Cl$, it is understood that other halogen exchange reactions, particularly when the catalyst used is an inorganic Cr (III) catalyst, would also benefit from the present improvement. Other halocarbons which may be used may be of the general formula $CA_3CH_2X$ where A is Br, Cl or F and X is Cl or Br. Such halocarbons include, among others, $CCl_3CH_2Cl$, $CFCl_2CH_2Cl$, $CF_2ClCH_2Cl$, $CCl_3CH_2Br$, $CFCl_2CH_2Br$, $CF_2ClCH_2Br$, $CF_3CH_2Br$, $CCl_2BrCH_2Br$, $CBr_2ClCH_2Cl$, $CHCl_2CHCl_2$, $CHFClCHCl_2$, $CHF_2CHCl_2$ and the like. The latter three rearrange during the course of the reaction.

The amount of hydrogen fluoride to be used in the present process depends upon the haloethane starting material. The molar ratio of hydrogen fluoride to haloethane should, in general, be at least equal to the number of halogen radicals of the haloethane to be replaced by fluorine radicals. Thus, when the reactant haloethane is $CF_3CH_2Cl$, at least one mol of HF per mol of $CF_3CH_2Cl$ is generally used. However, in order to enhance the exchange reaction and to minimize the formation of side products, an excess of HF may be used such that, with $CF_3CH_2Cl$ as a reactant, the ratio of hydrogen fluoride to $CF_3CH_2Cl$ is preferably from about 2:1 to about 15:1, more preferably in the range of from about 3:1 to about 10:1.

The inorganic chromium (III) catalysts used in the present process are well known in the art and can be prepared in a variety of ways. Such chromium (III) catalysts may be in the form of oxides, halides, oxyhalides and the like. The chromium (III) catalysts may be activated, for example, by heating in the presence of steam, an inert atmosphere or in the presence of hydrogen fluoride. The chromium (III) catalyst may be used in any convenient form, such as compressed into pellets, used in a fixed bed or, when in appropriate particle size, as fluidized beds or used on supports, such as carbon, alumina and the like.

Suitable temperatures for the present process are in the range of from about 300° C. to about 450° C., preferably in the range of from about 325° C. to about 400° C.

Contact time may be in the range of from about 2 seconds to about 150 seconds, preferably from about 15 seconds to about 120 seconds.

Atmospheric or superatmospheric pressures may be used, but superatmospheric pressures are preferred.

The concentration of chlorine in a chlorine-inert gas mixture may be any convenient amount and is not critical so long as at least some amount is present. By effective amount is meant an amount of chlorine in the co-feed which extends the period of catalyst activity beyond what it would be without the chlorine co-feed. Generally the amount of chlorine in the co-feed is in the range of from about 0.01 to about 1 mol percent of the 2-chloro-1,1,1-trifluoroethane in the reactant feed stream, preferably in the range of from about 0.03 to about 0.08, more preferably in the range of from about 0.06 to about 0.08 mol percent of the $CF_3CH_2Cl$ in the feed stream. For maximum effect, the chlorine co-feed should begin almost immediately after the feeds of hydrogen fluoride and 2-chloro-1,1,1-trifluoroethane into the reactor are started and maintained continuously.

Chlorine introduced into the reaction to prolong catalyst activity may be added as pure chlorine gas or may be introduced as gaseous mixtures with an inert gas such as nitrogen, depending upon the scale of the reaction. For large scale production, chlorine is preferably added as pure chlorine gas while on a smaller scale, the amount of chlorine introduced may be more readily controlled if a chlorine-inert gas mixture is used.

The desired product of the instant invention, 1,1,1,2-tetrafluoroethane ($CF_3CH_2F$) is useful as a refrigerant and as a propellant, particularly since it is not expected to play any role in stratospheric ozone depletion.

EXAMPLE 1

An Inconel schedule 40 U-tube reactor (1"×6') containing a thermocouple in the reaction zone was charged with about 900 ml of 20% $CrF_3$ on activated carbon as ¼" catalyst pellets. The U-tube was placed in a molten salt bath and connected to a feed system for feeding nitrogen, hydrogen fluoride, a mixture of hydrogen fluoride, 2-chloro-1,1,1-trifluoroethane and a 3.4% chlorine-in-nitrogen mixture. The exit from the U-tube was connected to a pressure control valve which was followed by a scrubbing system. The reaction product stream was analyzed by gas chromatography.

The catalyst bed was first dried by passing nitrogen gas through the reactor tube while the tube was heated to 330° C. at about 12 psig. Then hydrogen fluoride was introduced to saturate the catalyst bed.

A mixture of hydrogen fluoride and 2-chloro-1,1,1-trifluoroethane in a 3.8:1 molar ratio was fed to the catalyst bed. The contact time of this mixture with the catalyst was controlled by the feed rate at about 15 seconds. Very shortly after the feed of hydrogen fluoride and 2-chloro-1,1,1-trifluoroethane was started, another feed of a chlorine-nitrogen mixture was started to provide about 0.3 mol % chlorine based on the 2-chloro-1,1,1-trifluoroethane feed.

The production rate of 1,1,1,2-tetrafluoroethane was about 31 g per hour for 140 hours. Then the flow of chlorine-nitrogen was stopped, and almost immediately the production rate of 1,1,1,2-tetrafluoroethane began to drop such that, in the next 30 hours, the rate was about 21 g/hr or a drop in the production rate of about 32%.

EXAMPLE 2

Using the same equipment, catalyst and catalyst activation as described in Example 1, a feed of hydrogen fluoride/2-chloro-1,1,1-trifluoroethane was started at 330° C. and at about 160 psig to provide a contact time of about 112 seconds. The initial production rate of 1,1,1,2-tetrafluoroethane was 42 g/hr, but within 110 hours the production rate dropped to 3 g/hr or a drop in the production rate of almost 93%.

However, in a repeat of the above using a feed of hydrogen fluoride to 2-chloro-1,1,1-trifluoroethane of from 3.04 to 3.54 and chlorine-nitrogen co-feed to provide about 0.46 mol % chlorine, the production rate of 1,1,1,2-tetrafluoroethane remained at the level of 25–35 g/hr for 160 hours. Temporary interruption of the chlorine co-feed resulted in an immediate drop in the production rate. Resumption of chlorine co-feed maintained the production rate at about 20 g/hr for the next 90 hours. When the production rate dropped below 20 g/hr, the reaction temperature was incrementally raised over a 250-hour period to 395° C. to maintain the production rate at about 20 g/hr with chlorine co-feed.

EXAMPLE 3

The equipment described in Example 1 was used. The catalyst, used in about the same volume as in Example 1, was $Cr_2O_3$ prepared by pyrolysis of $(NH_4)_2Cr_2O_7$.

After drying and hydrogen fluoride saturation of the catalyst, hydrogen fluoride and 1,1,1-trifluoro-2-chloroethane in about 11.3 molar ratio was fed into the reactor to provide a contact time of about 16 seconds with the catalyst bed at 350° C. and 12 psig pressure, and chlorine-nitrogen mixture was immediately started to provide about 1 mol % chlorine. Over a period of 315 hours, the production rate of 1,1,1,2-tetrafluoroethane was in the range of 8–15 g/hr.

Under the same conditions with this catalyst but without the chlorine co-feed, the production rate of 1,1,1,2-tetrafluoroethane would have decreased to about zero in 300 hours.

I claim:

1. In a process for the manufacture of 1,1,1,2-tetrafluoroethane which comprises contacting, in the vapor phase at elevated temperature, a mixture of hydrogen fluoride and 2-chloro-1,1,1-trifluoroethane with an inorganic chromium (III) catalyst, the improvement comprising co-feeding an effective amount of elemental chlorine with said mixture of hydrogen fluoride and 2-chloro-1,1,1-trifluoroethane.

2. The process of claim 1 wherein said temperature is from about 300° C. to about 450° C., said mixture of hydrogen fluoride and 1,1,1-trifluoro-2-chloroethane is in molar ratio of hydrogen fluoride to 2-chloro-1,1,1-trifluoroethane of from about 2:1 to about 15:1 and said chlorine co-fee is from about 0.01 to 1 mol % chlorine based on the amount of 2-chloro-1,1,1-trifluoroethane.

3. The process of claim 2 wherein said chlorine co-feed is from about 0.03 to about 0.08 mol % chlorine based on the said 2-chloro-1,1,1-trifluoroethane.

4. The process of claim 3 wherein said temperature is from about 325° C. to about 400° C., said mixture of hydrogen fluoride and 2-chloro-1,1,1-trifluoroethane is in molar ratio of hydrogen fluoride to 2-chloro-1,1,1-trifluoroethane of from about 3:1 to about 0.08 and said chlorine co-feed is from about 0.06 to about 0.08 mol % chlorine based on the said 2-chloro-1,1,1-trifluoroethane.

* * * * *